(12) United States Patent
Schmidt

(10) Patent No.: US 6,782,290 B2
(45) Date of Patent: Aug. 24, 2004

(54) IMPLANTABLE MEDICAL DEVICE WITH RECHARGEABLE THIN-FILM MICROBATTERY POWER SOURCE

(75) Inventor: Craig Schmidt, Eagan, MN (US)

(73) Assignee: Medtronic, Inc., Minneapolis, MN (US)

( * ) Notice: Subject to any disclaimer, the term of this patent is extended or adjusted under 35 U.S.C. 154(b) by 130 days.

(21) Appl. No.: 09/843,673

(22) Filed: Apr. 27, 2001

(65) Prior Publication Data

US 2002/0161404 A1 Oct. 31, 2002

(51) Int. Cl.[7] .................................................. A61N 1/00
(52) U.S. Cl. .......................................... 607/2; 607/36
(58) Field of Search ............................... 607/2, 32–36, 607/60–61, 116; 604/891.1

(56) References Cited

U.S. PATENT DOCUMENTS

| | | |
|---|---|---|
| 4,096,866 A | 6/1978 | Fischell |
| 5,144,946 A | 9/1992 | Weinberg et al. |
| 5,338,625 A | 8/1994 | Bates et al. |
| 5,369,351 A | 11/1994 | Adams |
| 5,411,537 A | 5/1995 | Munshi et al. |
| 5,512,147 A | 4/1996 | Bates et al. |
| 5,561,004 A | 10/1996 | Bates et al. |
| 5,567,210 A | 10/1996 | Bates et al. |
| 5,569,520 A | 10/1996 | Bates |
| 5,597,660 A | 1/1997 | Bates et al. |
| 6,168,884 B1 | 1/2001 | Neudecker et al. |
| 6,273,904 B1 | 8/2001 | Chen et al. |
| 2002/0051551 A1 | 5/2002 | Leysieffer et al. |

FOREIGN PATENT DOCUMENTS

| | | |
|---|---|---|
| DE | 35 07 092 A1 | 8/1986 |
| EP | 1181952 A2 | 2/2002 |

OTHER PUBLICATIONS

Bates, John B. et al., "Thin Film Rechargeable Lithium Batteries for Implantable Devices", *ASAIO Journal*, J.B. Lippincott Co., Hagerstown, MD, US, vol. 43, No. 5, Sep. 1, 1997, pp. 644–647.

*Primary Examiner*—Mark Bockelman
(74) *Attorney, Agent, or Firm*—Banner & Witcoff, Ltd.

(57) ABSTRACT

The present invention is an implantable medical device comprising an outer housing, electronics within the outer housing, the electronics located in on a substrate circuit board, and a rechargeable thin-film microbattery within the outer housing. The rechargeable thin-film microbattery of the present invention is a solid-state battery that is devoid of liquids or other volatile materials from which the electronics must be protected. In one embodiment, the rechargeable thin-film microbattery has a straight first side that is adjacent to the substrate circuit board, and a curved second side that is adjacent to the outer housing. In one embodiment, the rechargeable thin-film microbattery lies in a plane that is parallel to the substrate circuit board containing the electronics. In one embodiment, the electronics are on a first face of the substrate circuit board, and the rechargeable thin-film microbattery is positioned adjacent a second face of the substrate circuit board, the second face being on the side of the substrate circuit board opposite to the first face. In one embodiment, the rechargeable thin-film microbattery is deposited on the bottom face of the substrate circuit board. In one embodiment, the may be two or more microbatteries that are stacked in series or in parallel.

28 Claims, 7 Drawing Sheets

IMPLANTABLE MEDICAL DEVICE WITH RECHARGEABLE THIN-FILM MICROBATTERY POWER SOURCE

FIELD OF THE INVENTION

The invention relates to implantable medical devices having rechargeable thin-film microbattery power sources.

BACKGROUND OF THE INVENTION

Current implantable medical devices require an electrical power source that contains one or more volatile components. These volatile components must be effectively contained in the battery throughout the life of the medical device. Typically, the volatile component is a liquid electrolyte. However, it may also be a cathode material as in the lithium/iodine battery, or a combined electrolyte/cathode ("catholyte"), as in a lithium/thionyl chloride battery. In any case, leakage of these materials will cause catastrophic failure of the circuit or electronics of the device.

Typically, the volatile components are contained by housing the active battery materials in a corrosion resistant metal case. The metal case is usually hermetically sealed either through a crimped seal with a polymer gasket, or by a welded seal. In the latter case, at least one electrical feedthrough (also hermetic) is required to access one electrode of the battery. The second electrode is often accessed by contact with the hermetic, metallic enclosure of the battery. The feedthrough is a relatively expensive component, requires extensive internal insulation, and is volumetrically inefficient.

Both crimped-seal battery enclosures and welded battery enclosures require verification of hermetic seal integrity. With a crimped-seal battery, this is typically accomplished by storing the battery for a period of approximately 30 to 45 days, and then visually inspecting for signs of leakage (i.e., salt crystal formation or corrosion). This is a highly undesirable process due to the long manufacturing cycle time and the large delay between the initiation and detection of any issue with seal integrity. In addition to the need for and difficulty in verifying the integrity of the seal, crimped-seal batteries typically require a circular shape that is difficult to package efficiently in an implantable medical device because of unused space at the "corners" when the circular shaped device is placed in the medical device and adjacent to the substrate circuit board upon which the electronics are located.

Welded-seal batteries are typically subjected to a leak test procedure prior to filling with electrolyte, and then tested again after the final seal is welded in place. The first leak check is accomplished by pulling a vacuum on the welded battery case and cover through the electrolyte fill port while spraying helium on the exterior of the case. If helium leaks into the interior of the case, it is detected by a mass spectrometer. The second (final) leak check is more complicated. After the battery is filled with electrolyte (or cathode or catholyte) through a specially designed fill port, a temporary plug-type seal is placed deep in the fill port. The area above the temporary seal is either void volume or filled with a material that can absorb helium (e.g., very small porous glass spheres). A final seal is then welded in place at the entrance to the fill port, leaving a void volume or the helium absorbing material between the temporary seal and the final seal. The sealed battery is then placed in a helium atmosphere at a specified pressure for a specified time. If the final seal is not hermetic, helium will leak into the space between the two seals. The battery is then placed in an enclosure and a vacuum is pulled on the enclosure. If the final seal is not adequate, helium will leak from the fill port into the enclosure and be detected as described earlier.

Furthermore, liquid electrolyte batteries, have several added disadvantages that typically include the following: (1) a porous cathode filled with liquid electrolyte (which is volumetrically inefficient); (2) a porous or ion-conductive separator of sufficient dimension to prevent shorting by foreign particles (typically two layers of 0.001" or greater); (3) a large headspace for additional liquid electrolyte (porous cathodes often swell during discharge and require additional electrolyte to ensure that they remain immersed in liquid electrolyte); (4) a large headspace to allow for appropriate electrical insulation to provide isolation of positive and negative terminals of the battery and to provide thermal insulation to prevent damage to the active components during welding of the battery enclosure, which is typical for liquid electrolyte batteries; and (5) conductive diluents to make the cathode material electrically conductive and binders to hold cathode material together, which comprise about 10% to 15% by weight of the cathode.

Crimped-seal and welded-seal batteries have several limitations with respect to geometry and physical dimensions. For example, crimped-seal designs are typically limited to circular shapes (a thin disk or cylinder). These shapes do not package efficiently in implantable devices and tend to result in a large amount of unusable volume. It also becomes very difficult to attain an adequate seal as the dimension of the seal area increases. Hence, it is difficult to build a thin, disk-shaped battery with a large diameter. Thin, large surface-area welded-seal batteries are also difficult to manufacture. Thinness is often limited by feedthrough dimensions, and surface area is limited by electrode handling properties and/or the tolerances of the case and cover materials.

Welded-seal rechargeable batteries are typically prismatic, i.e., they are rectangular prism shaped batteries with 90 degree corners. A problem with such batteries is that they do not have a curved shape, which is desirable in an implantable medical device (except for the disadvantage of unused space as previously described above for circular shaped batteries when placed adjacent to a substrate circuit board within the device).

Figure 1A:
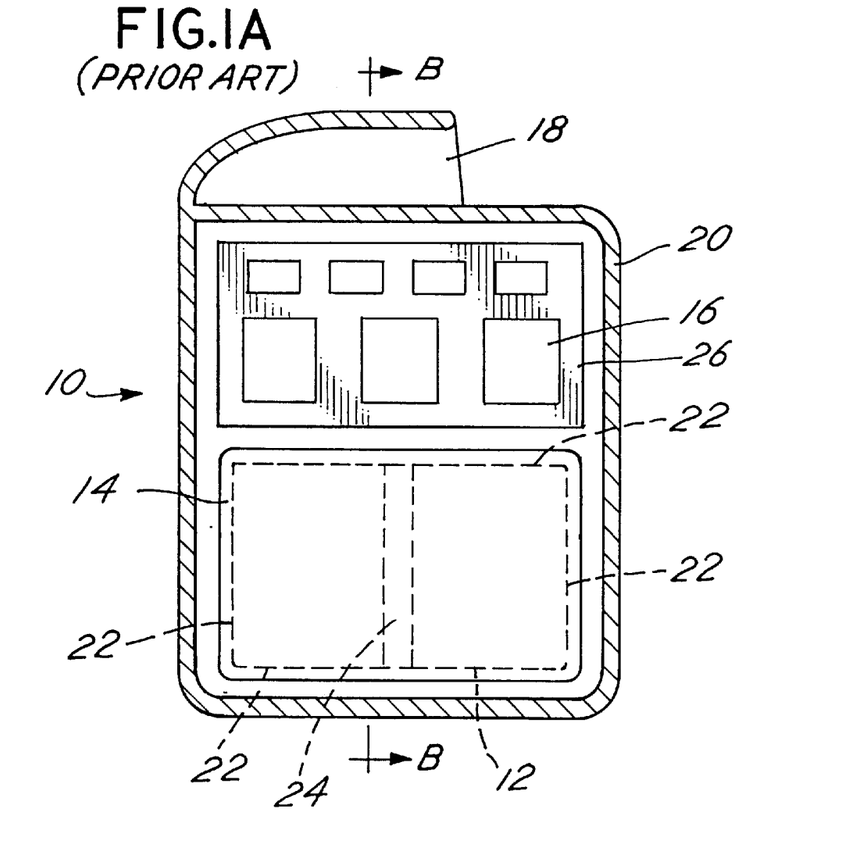
FIG. 1A is a top cut-away view of a conventional implantable medical device having a prismatic battery containing a liquid electrolyte.
Figure 1B:
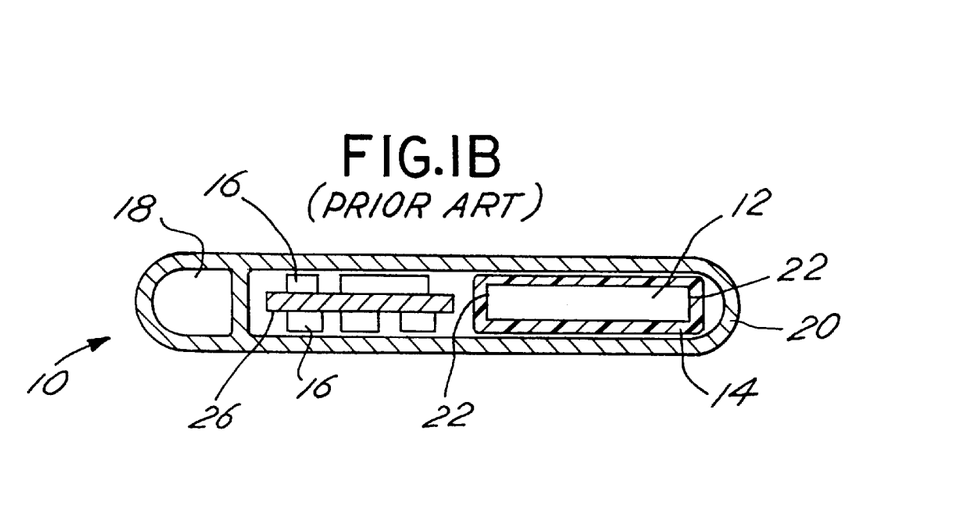
FIG. 1B is a cross-sectional view of the conventional implantable medical device shown in FIG. 1A taken along line B—B.

An example of a conventional implantable medical device having a prismatic battery having a liquid electrolyte is shown in FIGS. 1A and 1B. Referring to the drawings, FIG. 1A is a top cut-away view of a conventional implantable medical device 10. Device 10 has a rechargeable battery 12 that is placed in a hermetic case 14. Device 10 also has electronics 16. Hermetic case 14 protects the electronics 16 from the liquid electrolyte (not shown) in rechargeable battery 12. Device 10 also has a connector block 18 that is used to provide an electrical connection between device 10 and electrodes (not shown), which provide electrical stimulation to patient tissue. Device 10 has a shield 20 and a cover (not shown). As shown, battery 12 has straight sides 22. Separator 24 is used to provide a physical barrier that is needed between the anode and the cathode (not shown) in battery 12 since it has a liquid electrolyte. Electronics 16 are located on a substrate circuit board 26. Device 10 also has a coil of wire for charging the battery 12 via induction. The coil (not shown), can be located either internal or external to device 10. FIG. 1B is a cross-sectional view of the conventional implantable medical device 10 taken along line B—B in FIG. 1A.

Figure 1C:
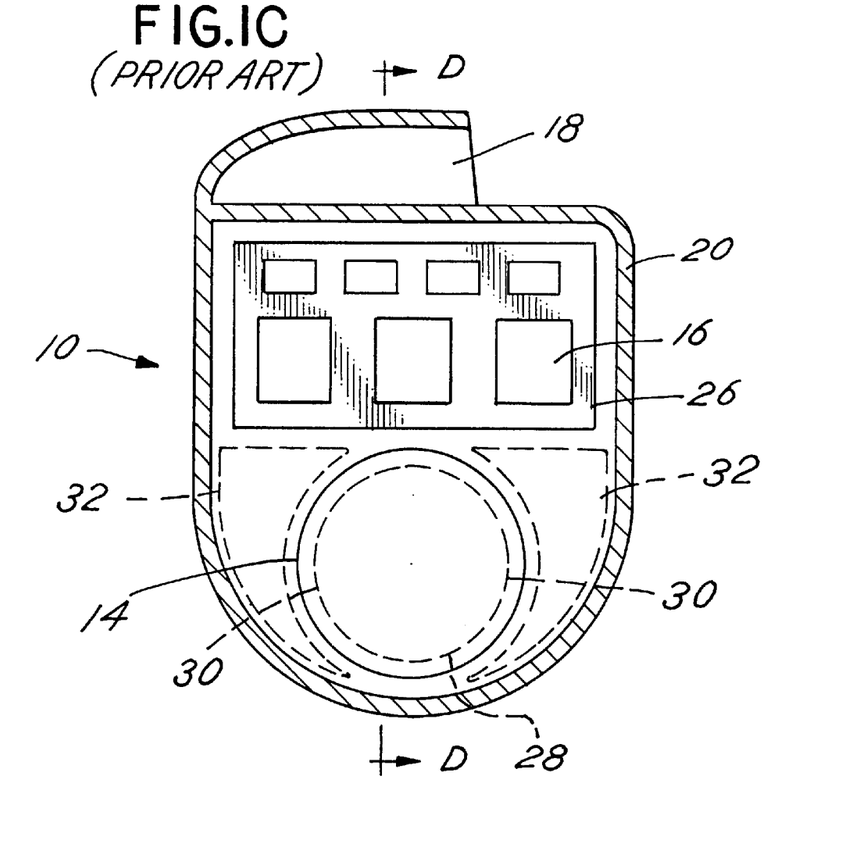
FIG. 1C is a top cut-away view of a conventional implantable medical device having a circular battery containing a liquid electrolyte.
Figure 1D:
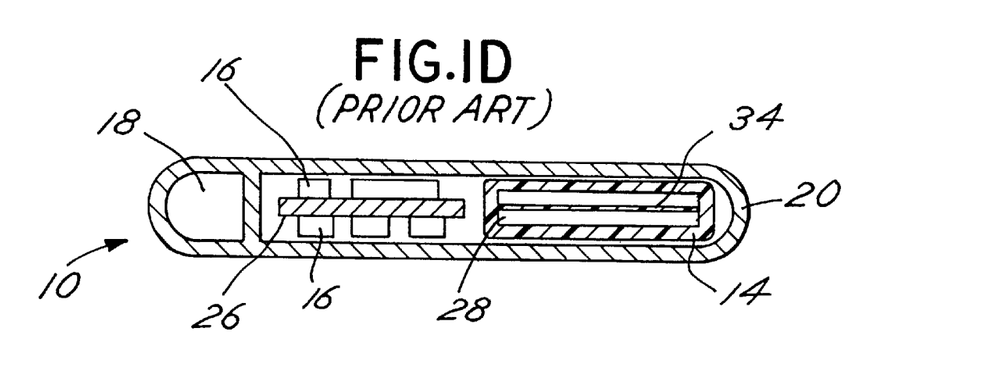
FIG. 1D is a cross-sectional view of the conventional implantable medical device shown in FIG. 1C taken along line D—D.

An example of a conventional implantable medical device having a circular battery with a liquid electrolyte is shown in FIGS. 1C and 1D. Referring to the drawings, FIG. 1C is a top cut-away view of a conventional implantable medical device 10. Device 10 has a rechargeable circular battery 28 that is placed in a hermetic case 14. Device 10 also has electronics 16. Hermetic case 14 protects the electronics 16 from the liquid electrolyte (not shown) in rechargeable battery 28. Device 10 also has a connector block 18 that is used to provide an electrical connection between device 10 and electrodes (not shown), which provide electrical stimulation to patient tissue. Device 10 has a shield 20 and a cover (not shown). As shown, battery 28 has a continuous curved side 30. Separator 34 is used to provide a physical barrier that is needed between the anode and the cathode (not shown) in battery 28 since it has a liquid electrolyte. As shown in FIG. 1C, unused space 32 exists because the battery 28 having a circular side 30 does not fill reach the unused space 32 defined by the battery 28, shield 20 and substrate circuit board 26. Unused space 32 is one of the important disadvantages in this conventional device. Electronics 16 are located on a substrate circuit board 26. Device 10 also has a coil of wire for charging the battery 28 via induction. The coil (not shown), can be located either internal or external to device 10. FIG. 1D is a cross-sectional view of the conventional implantable medical device 10 taken along line D—D in FIG. 1C.

SUMMARY OF THE INVENTION

The present invention is an implantable medical device comprising an outer housing, electronics within the outer housing, the electronics located in on a substrate circuit board, and a rechargeable thin-film microbattery within the outer housing. The rechargeable thin-film microbattery of the present invention is a solid-state battery that is devoid of liquids or other volatile materials from which the electronics must be protected.

In a preferred embodiment, the rechargeable thin-film microbattery has a straight first side that is adjacent to the substrate circuit board, and a curved second side that is adjacent to the outer housing.

In a preferred embodiment, the rechargeable thin-film microbattery lies in a plane that is parallel to the substrate circuit board containing the electronics. In a preferred embodiment, the electronics are on a top side or first face of the substrate circuit board, and the rechargeable thin-film microbattery is positioned underneath a bottom side or second face of the substrate circuit board, the second face being on the side of the substrate circuit board opposite the first face. In a further preferred embodiment, the rechargeable thin-film microbattery is deposited on the bottom side of the substrate circuit board.

In another preferred embodiment, the rechargeable thin-film microbattery lies in a plan that is parallel to the substrate circuit board and the device includes a back-up battery adjacent to the circuit board and the rechargeable thin-film microbattery.

In an alternative preferred embodiment, a first group of the electronics is located on a first face of the substrate circuit board, and a second group of electronics is located on a second face of the electronics are located on the bottom side of the substrate circuit board, and the rechargeable thin-film microbattery is located underneath or over a back-up battery, and both batteries are located adjacent to the substrate circuit board.

In an alternative preferred embodiment, the rechargeable thin-film microbattery lies in a plane that is parallel to the substrate circuit board, the electronics are located on the a first face or the first face and the second face of the substrate circuit board, and the microbattery is positioned adjacent the second face of the substrate circuit board and is adjacent to at least a portion of a back-up battery that is adjacent to the substrate circuit board.

DETAILED DESCRIPTION OF THE INVENTION

Figure 2A:
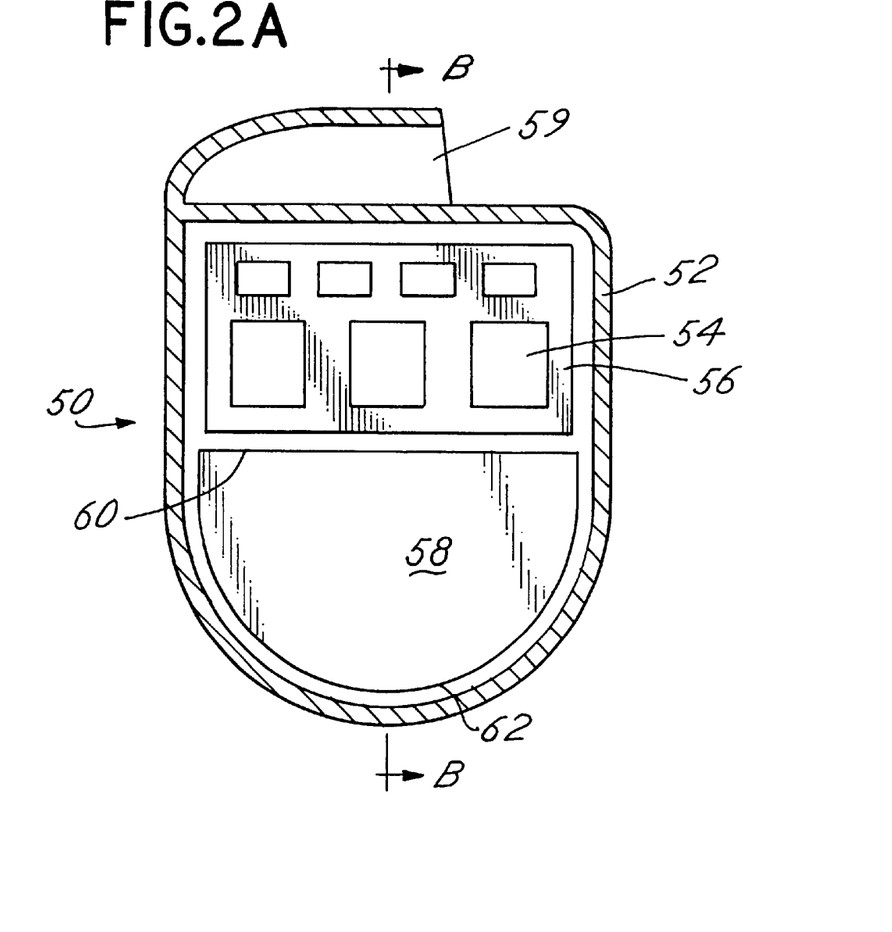
FIG. 2A is a top cut-away view of a preferred embodiment of the implantable medical device of the present invention.
Figure 2B:
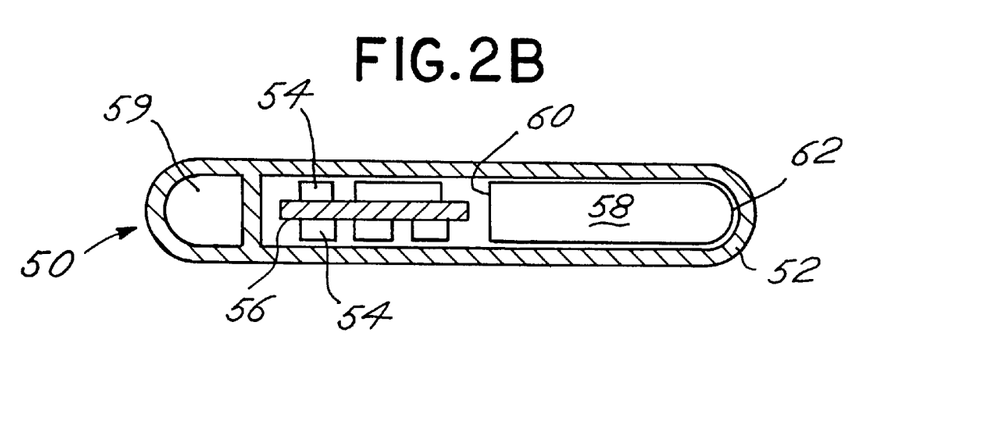
FIG. 2B is a cross-sectional view of a preferred embodiment of the implantable medical device of the present invention shown in FIG. 2A taken along line B—B.

FIGS. 2A and 2B illustrate a preferred embodiment of the present invention. As shown, an implantable medical device 50 comprises an outer housing 52, electronics 54 within the outer housing 52, the electronics 54 located on a substrate circuit board 56, and a rechargeable thin-film microbattery 58 within the outer housing 52. The rechargeable thin-film microbattery 58 of the present invention is a solid-state battery that is devoid of liquids or other volatile materials from which the electronics must be protected.

In the embodiment shown in FIGS. 2A and 2B, the rechargeable thin-film microbattery 58 has a straight first side 60 that is adjacent to the substrate circuit board 56, and a curved second side 62 that is adjacent to the outer housing 52. As shown in FIGS. 2A and 2B, the rechargeable thin-film battery 58 has a "D" shape. This "D" shape retains the curved outer edge desirable for an implantable medical device (which is not achieved with a conventional device having a liquid electrolyte, prismatic battery shown in FIGS. 1A and 1B), while at the same time, avoids unused space resulting from using a circular battery in a conventional device (shown in FIGS. 1C and 1D). Device 50 also has a connector block 59 that is used to provide an electrical connection between device 50 and electrodes (not shown), which provide electrical stimulation to patient tissue. Device 50 has a cover (not shown) for the outer housing 52. Device 50 also has a coil of wire for charging the battery 58 via induction. The coil (not shown), can be located either internal or external to device 50.

Since the rechargeable thin-film battery 58 in device 50 is a solid-state battery, no separator is required to provide a physical barrier between the anode and the cathode (not shown) in battery 58 to account for the presence of a liquid electrolyte. In addition, since the rechargeable thin-film battery 58 in device 50 is a solid-state battery, there is no need for a hermetic seal to protect the electronics 54 from a liquid electrolyte, as is required in conventional medical devices. By removing the need for a separator and a hermetic seal, the present invention provides a medical device with a desired shape and less unused space.

In the embodiment shown in FIG. 2B, electronics 54 are located on both sides of substrate circuit board 56. FIG. 2B is a cross-sectional view of the conventional implantable medical device 50 shown in FIG. 1A.

Figure 3A:
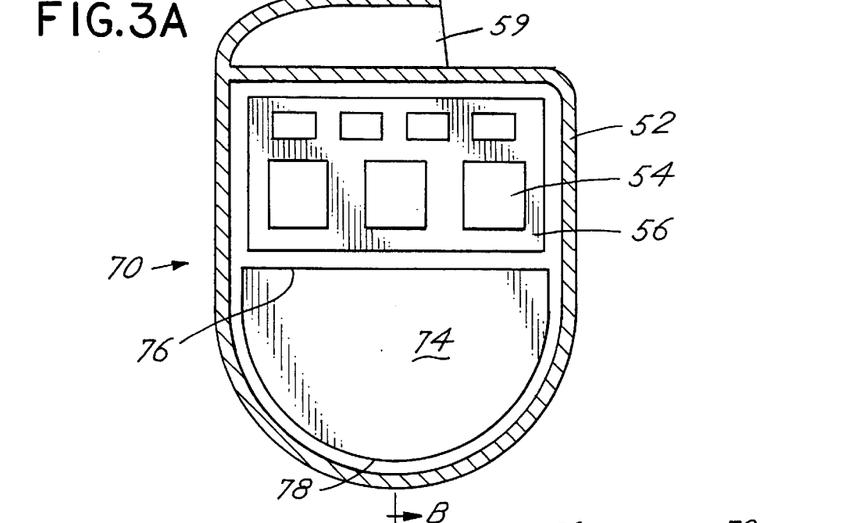
FIG. 3A is a top cut-away view of a preferred embodiment of the implantable medical device of the present invention.
Figure 3B:
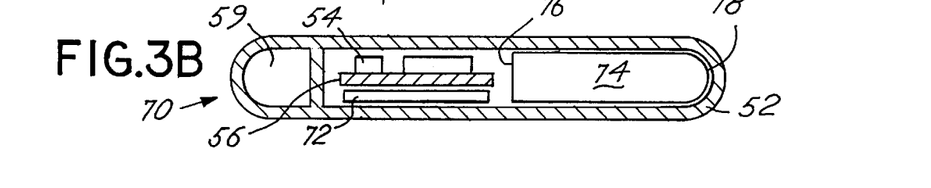
FIG. 3B is a cross-sectional view of a preferred embodiment of the implantable medical device of the present invention shown in FIG. 3A taken along line B—B.

An alternative embodiment is shown in FIGS. 3A and 3B. The embodiment shown in FIGS. 3A and 3B illustrates a device 70, a rechargeable thin-film microbattery 72, and a primary or back-up battery 74. Microbattery 72 is positioned underneath substrate circuit board 56. Microbattery 72 can be deposited onto substrate circuit board 56 if desired. Backup battery 74 can be rechargeable if desired. Back-up battery 74 can be made in the same manner as microbattery 72. Alternatively back-up battery 74 can be a non-rechargeable battery and easily packaged as a lower power source. As shown in FIG. 3B, back-up battery 74 can have a straight side 76 adjacent to the substrate circuit board 56 and the microbattery 72. As further shown in FIGS. 3A and 3B, back-up battery 74 can have a curved side 78 adjacent to the outer housing 52. Device 70 further has electronics 54 on substrate circuit board 56, and a connector block 59 as previously described. Back-up battery 74 may be particularly desirable in a medical device that is used for life support of a patient. If desired, back-up battery 74 can serve as a power source for a particular electrical requirement, e.g., for electrical stimulation to the patient, and microbattery 72 can serve as a power source for a different particular electrical requirement.

Figure 3C:
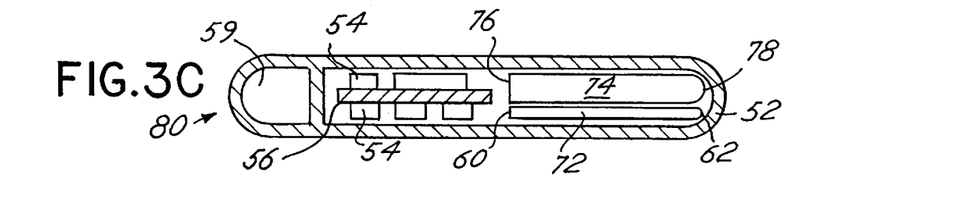
FIG. 3C is a cross-sectional view of an alternative preferred embodiment of the implantable medical device of the present invention shown in FIG. 3A taken along line B—B.

Another embodiment of the present invention is shown for device 80 in FIG. 3C. The embodiment shown in FIG. 3C is similar to the embodiment shown in FIG. 3B, except microbattery 72 is positioned underneath back-up battery 74. Microbattery 72 can have a straight side 60 adjacent to substrate circuit board 56, and back-up battery 74 can have a straight side 76 adjacent to substrate circuit board 56. Microbattery 72 can have a curved side 62 adjacent to outer housing 52, and back-up battery 74 can have a curved side 78 adjacent outer housing 52. In FIG. 3C, electronics 54 are positioned above and below substrate circuit board 56.

Figure 3D:
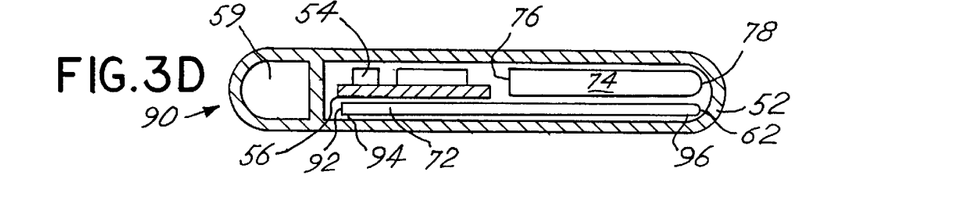
FIG. 3D is a cross-sectional view of another alternative preferred embodiment of the implantable medical device of the present invention shown in FIG. 3A taken along line B—B.

Another embodiment of the present invention is shown for device 90 in FIG. 3D. The embodiment shown in FIG. 3D is similar to the embodiments shown in FIGS. 3B and 3C, except microbattery 72 is positioned underneath back-up battery 74 and substrate circuit board 56. Microbattery 72 can have a straight side 92 at a first end 94 of the microbattery and adjacent to substrate circuit board 56. Back-up battery 74 can have a straight side 76 adjacent to substrate circuit board 56. Microbattery 72 can have a curved side 62 adjacent to outer housing 52 at a second end 96 of microbattery 72. Back-up battery 74 can have a curved side 78 adjacent outer housing 52. In FIG. 3D, electronics 54 are positioned above substrate circuit board 56.

Figure 3E:
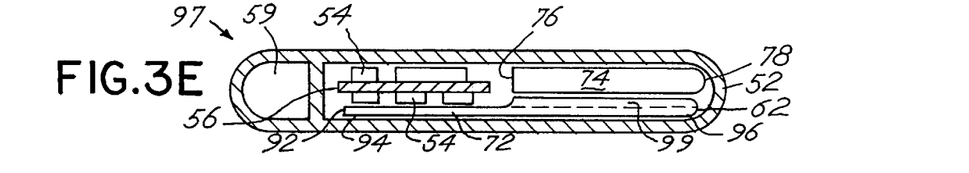
FIG. 3E is a cross-sectional view of another alternative preferred embodiment of the implantable medical device of the present invention shown in FIG. 3A taken along line B—B.

Another embodiment of the present invention is shown for device 97 in FIG. 3E. The embodiment shown in FIG. 3E is similar to the embodiments shown in FIGS. 3B, 3C, and 3D, except microbattery 72 is positioned underneath back-up battery 74 and substrate circuit board 56, and electronics 54 are positioned both above and below substrate circuit board 56. Additional portion 99 for microbattery 72 is shown underneath back-up battery 74 since there are no electronics 54 at this location in the device 97. Alternatively, a corresponding portion (not shown) can be added to back-up battery 74 instead of additional portion 99 for microbattery 72. Microbattery 72 can have a straight side 92 at a first end 94 of microbattery 72 and adjacent to substrate circuit board 56. Back-up battery 74 can have a straight side 76 adjacent to substrate circuit board 56. Microbattery 72 can have a curved side 62 adjacent to outer housing 52 at a second end 96 of microbattery 72. Back-up battery 74 can have a curved side 78 adjacent outer housing 52. In FIG. 3C, electronics 54 are positioned above and below substrate circuit board 56.

Figure 4A:
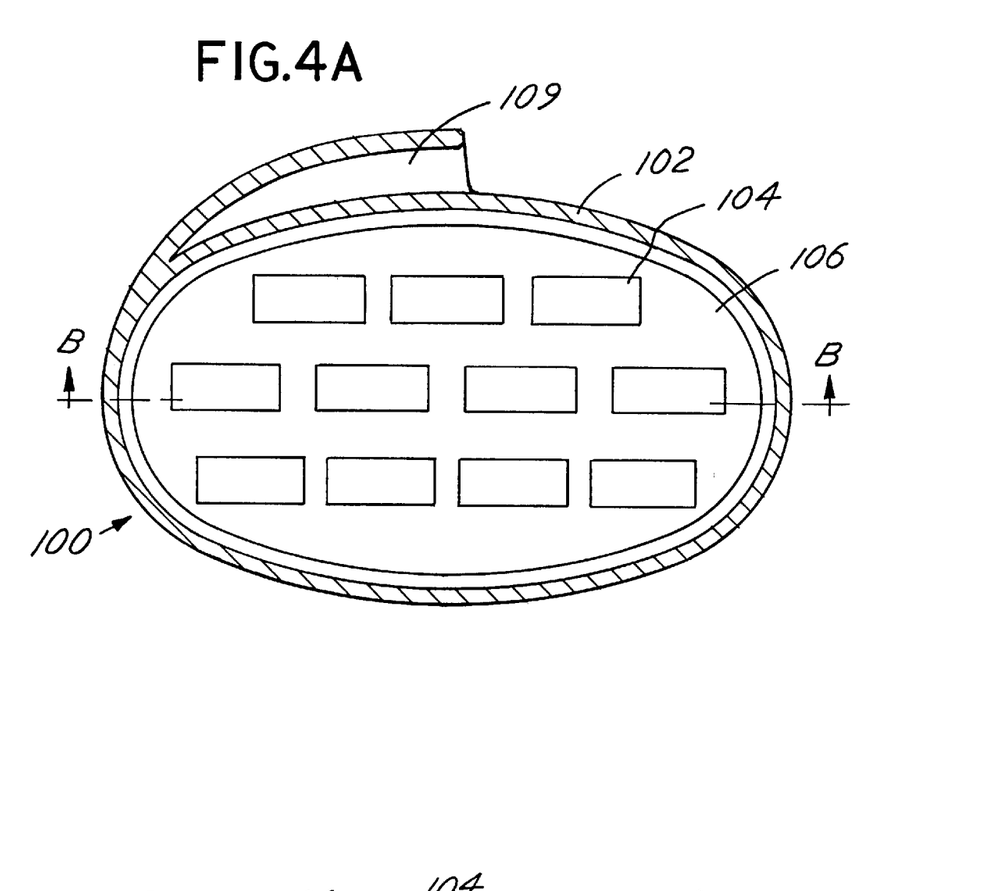
FIG. 4A is a top cut-away view of an alternative preferred embodiment of the implantable medical device of the present invention.
Figure 4B:
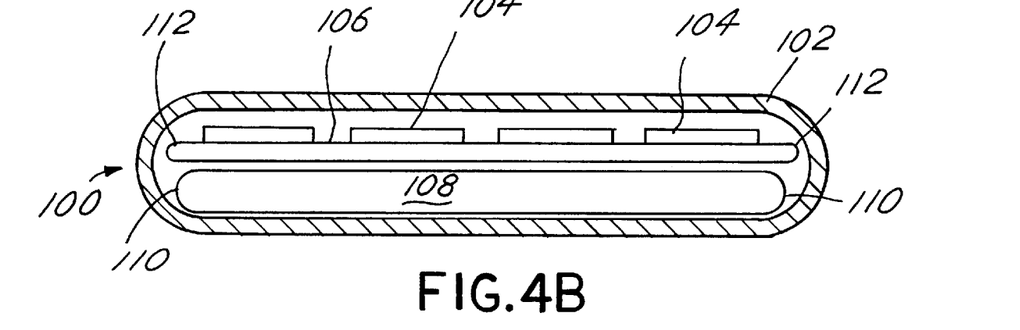
FIG. 4B is a cross-sectional view of an alternative preferred embodiment of the implantable medical device of the present invention shown in FIG. 4A taken along line B—B.

Another embodiment of the present invention is shown in FIGS. 4A and 4B. In the embodiment shown, a device 100 has an outer housing 102, a substrate circuit board 106, and electronics 104 on the substrate circuit board. Device 100 further has a rechargeable thin-film microbattery 108 underneath substrate circuit board 106. Preferably, the substrate circuit board 106 and the microbattery 108 are oval in shape. Microbattery 108 can have a curved side 110, and substrate circuit board 106 can have a curved side 112, which are shown in FIGS. 4A and 4B. Device 100 can have a connector block 109 that serves the same function and purpose as connector block 59 in FIGS. 2A, 2B, 3A, 3B, 3C, 3D, and 3E. FIG. 4B is a cross-sectional view of device 100 taken along line B—B in FIG. 4A.

Figure 5A:
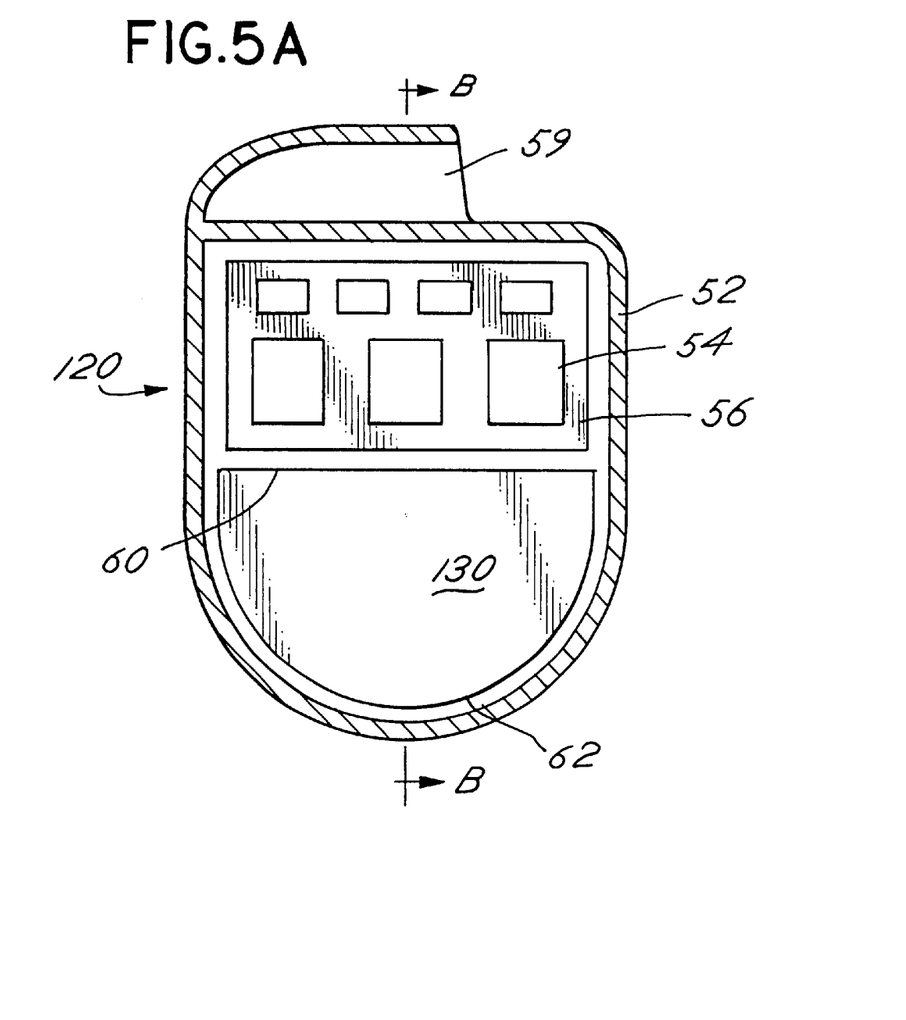
FIG. 5A is a top cut-away view of an alternative preferred embodiment of the implantable medical device of the present invention.
Figure 5B:
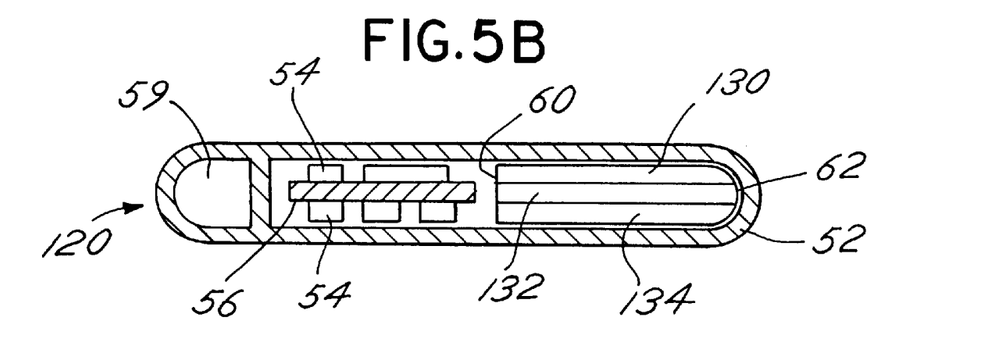
FIG. 5B is a cross-sectional view of an alternative preferred embodiment of the implantable medical device of the present invention shown in FIG. 5A taken along line B—B.

Another embodiment of the present invention is shown in FIG. 5. The device 120 shown in FIG. 5 is the same as the device 50 shown in FIGS. 2A and 2B, except that instead of a single microbattery 58, the device now has two or more microbatteries that are stacked. As shown in FIG. 5, device 120 has three microbatteries 130, 132, and 134 that are stacked.

Figure 6A:
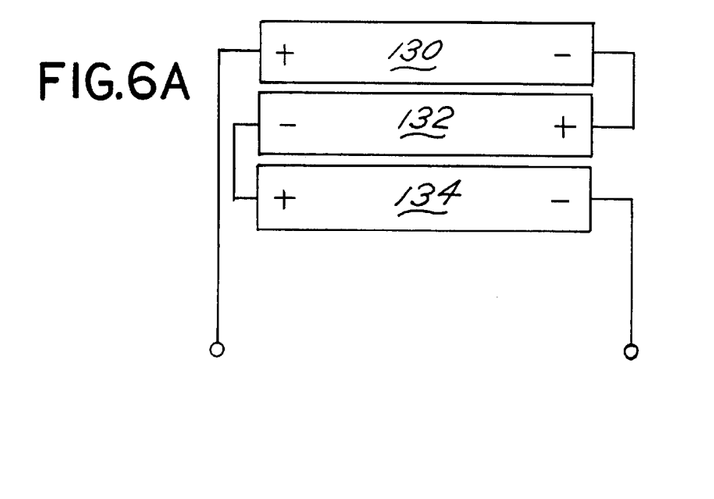
FIG. 6A is a cross-sectional view of stacked microbatteries in a series configuration in accordance with the present invention.
Figure 6B:
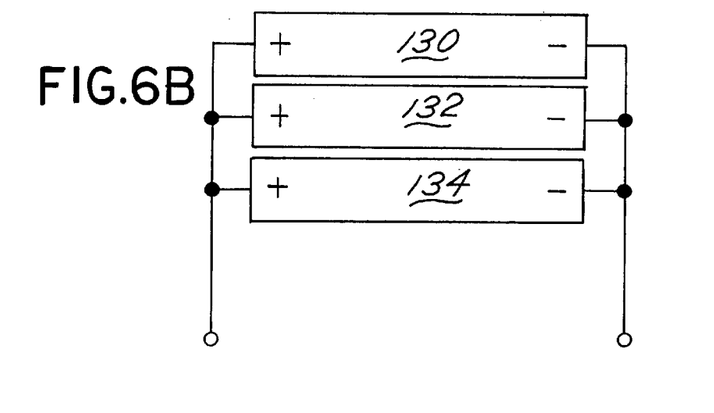
FIG. 6B is a cross-sectional view of stacked microbatteries in a parallel configuration in accordance with the present invention.
Figure 6C:
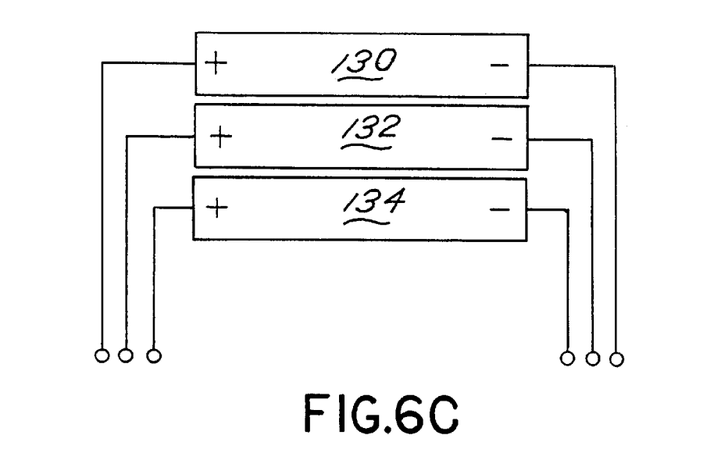
FIG. 6C is a cross-sectional view of stacked microbatteries in a dynamically reconfigureable arrangement.

If desired, the stacked microbatteries 130, 132, 134 can be connected in either a series configuration 140 (shown in FIG. 6A) or a parallel configuration 142 (shown in FIG. 6B). This flexibility in configuration of stacked microbatteries is an additional advantage of the present invention over the conventional device. It is also possible to design a dynamically reconfigureable arrangement 144 (shown in FIG. 6C). Arrangement 144 can be used to create a series connection, a parallel connection, or combination of series and parallel connections between the individual microbatteries. The result is a battery configuration that can comprise a variety of voltage and capacity combinations. For example, three 4 volt microbatteries can be configured in a parallel configuration for charging, and then reconfigured in a series configuration via device programming to create a 12 volt microbattery for discharge, or vice-a-versa.

The ability to dynamically create a higher voltage battery is an advantage when the voltage at the stimulation site is greater than the voltage of that of a single cell (i.e., 4 volts in the example above). In current medical devices, this multiplication of battery voltage is typically achieved by dynamically reconfigureable capacitors. The capacitors are charged in parallel to the voltage of the single cell battery, and then are reconfigured in series to create the desired stimulation voltage. The dynamically reconfigureable battery of the present invention eliminates the capacitor components required for reconfiguration, thereby creating a simpler, and more volumetrically efficient device.

In a preferred embodiment, the rechargeable thin-film microbattery lies in a plane that is parallel to the substrate circuit board containing the electronics. In a preferred embodiment, the electronics are on a top side of the substrate circuit board, and the rechargeable thin-film microbattery is positioned underneath a bottom side of the substrate circuit board. In a further preferred embodiment, the rechargeable thin-film microbattery is deposited on the bottom side of the substrate circuit board.

In an alternative embodiment, the rechargeable thin-film microbattery lies in a plan that is parallel to the substrate circuit board and the device includes a back-up battery adjacent to the circuit board and the rechargeable thin-film microbattery.

In an alternative embodiment, some of the electronics are located on the top side of the substrate circuit board, and some of the electronics are located on the bottom side of the substrate circuit board, and the rechargeable thin-film microbattery is located underneath or over the back-up battery, and both batteries are located adjacent to the substrate circuit board.

In an alternative embodiment, the rechargeable thin-film microbattery lies in a plane that is parallel to the substrate circuit board, and the microbattery is positioned underneath a bottom side of the substrate circuit board and is underneath at least a portion of a back-up battery that is adjacent to the substrate circuit board.

The present invention provides many advantages over current implantable medical devices, including but not limited to: (1) an implantable medical device with a power source devoid of volatile components; (2) an implantable medical device with a power source that does not require an independent, hermetic compartment within the an implantable medical device to separate the power source from other components of the device; (3) increased design flexibility since the power source of the implantable medical device can be configured in a wide variety of shapes, including thin film shapes that can overlay other components of the implantable medical device, such as a microprocessor and/or electronic circuitry; (4) an implantable medical device with greater volumetric efficiency (that is, more electrical power without increasing the size of the implantable medical device); (5) simpler manufacturing steps to make an implantable medical device; (6) elimination of electrical feedthroughs between the power source and the electronics; and (7) elimination of need to check against leaks of battery liquids (that is, verification of seal integrity).

The thin-film battery of the present invention can be made in accordance with methods taught in U.S. Pat. Nos. 5,338, 625, 5,561,004, and 6,168,884 (all of which are incorporated herein by reference).

In a preferred embodiment, the thin-film battery may incorporate a protective coating to protect the power source from ambient conditions (particularly moisture) prior to assembly of the power source into the implantable medical device. Such a coating is described in U.S. Pat. No. 5,561, 004 (which is incorporated herein by reference). However, coatings such as this are not hermetic and are intended merely to provide a temporary protection of the battery materials from the atmosphere, not protection of the electronics from the battery materials. Alternate forms of the thin film battery that do not contain metallic lithium prior to the first charge of the battery may not require a protective coating (e.g., the battery disclosed in U.S. Pat. No. 6,168, 884).

The implantable medical devices of the present invention provide the following advantages over typical implantable medical devices with respect to volumetric efficiency: (1) no separator is required—the thin layer of solid-state electrolyte provides the separator function; (2) no conductive diluents or binders are required—the cathode is 100% active; (3) there is no need for "excess" liquid electrolyte to cover the cathode and the anode; (4) no electrical feedthroughs are required between the thin-film battery and the electronics; and (5) there is no separate battery case since the battery can be deposited on a thin substrate.

The implantable medical device of the present invention provides the following advantages over typical implantable medical devices with respect to packaging: (1) the design shape of the power source is not limited to circular shapes (such as a thin disk or cylinder), which is a shape that does not package efficiently in implantable medical devices and tend to result in a large amount of unusable volume within the device; (2) there is no need to achieve an adequate seal as the dimension of the seal area increases, and thus it is easier to build a thin-film battery with a large surface area; and (3) the thinness of the power source is not as limited by feedthrough dimensions, electrode handling properties or tolerances of the case and cover materials as the prior art devices.

Thus, the thin-film batteries of the present invention provide the certain advantages with respect to thinness and efficient packaging. For example, in the present invention, active materials are deposited on a thin substrate that can be large in surface area. In some cases, a limited degree of substrate flexibility may also be possible. When larger capacities are required, it may be possible to deposit several layers of active materials or stack and interconnect several cells, each deposited on its own substrate. The deposit of several layers of active materials may be accomplished in accordance with the methods disclosed in U.S. Pat. No. 5,569,520, which is incorporated herein by reference.

In addition, the substrate has essentially unlimited shape flexibility, thereby allowing the battery to fit efficiently into the shape of the implanted device. In accordance with the present invention, smaller medical devices can be designed so that they can be placed within a human being closer to a target site than are possible with current medical devices. By placing the medical device closer to the target site, less problems in transfer of electrical stimulation therapy are encountered.

Further, smaller medical devices can be designed so that they can be placed within a human being at a location that will be less noticeable or not noticeable by a viewer looking at the human who has the implanted medical device.

The thinness of battery and substrate in accordance with the present invention allows the battery to be stacked with other components. For example, the rechargeable thin-film battery of the present invention may be stacked with a back-up battery, stacked with the circuit, or located across the entire shield of the implanted device (i.e., stacked with all components).

In addition, the active materials can be placed directly onto the same substrate as the circuit components. A substrate can be populated by circuit components on one side of the substrate, and by active battery materials on the other side of the substrate.

The present invention also provides advantages over current implantable medical devices with respect to the charging coil. Currently, rechargeable batteries in implantable medical devices involve recharging by induction. This requires incorporation of a secondary coil in the implanted medical device. Typically, the coil is a discrete component that is wound from wire and located either internal to the device or encased in polymer and located on an external surface of the device.

In accordance with the present invention, it may be possible to deposit a coil on the same substrate as the battery. This could be accomplished at the same time that the current collectors and contacts are being deposited for the battery.

The present invention also provides manufacturing advantages over the manufacturing methods of conventional implantable medical devices. More specifically, the fabrication of the battery and device can be more easily automated and justified for smaller volumes. As previously noted, the batteries can be fabricated on the same substrate as the circuit. Further, the battery can be exposed to solder-reflow conditions without damage. See U.S. Pat. No. 6,168,884, which is incorporated herein by reference.

In addition, conventional rechargeable batteries suffer from several characteristics that limit their usefulness in implantable medical devices, including: (1) cycle-dependant capacity fade (in other words, upon repeated charge/discharge cycles, the useable capacity of the battery gradually declines); (2) limited useful cycle life (most rechargeable batteries range from about 300 to 1500 cycles); (3) time-dependant capacity fade (even without charge/discharge cycling, the useable capacity of the battery declines over time due to a variety of loss mechanisms—most rechargeable batteries have a lifetime of only a few years when used under the most ideal circumstances; (4) history-dependant capacity fade ("memory effect"; many rechargeable batteries suffer a loss of usable capacity if they are not fully charged and discharged. The requirement to fully charge and discharge a battery is highly undesirable in an implanted device.)

Thus, the implantable medical device of the present invention provides the following further advantages over conventional devices: (1) nearly unlimited cycle life—Charge/discharge cycles in excess of 50,000 have been demonstrated; (2) little or no time-dependent capacity loss; and (3) no "memory effect."

The present invention has been described in detail with particular reference to certain preferred embodiments thereof, and those of skill in the art will appreciate that variations and modifications are within the spirit and scope of the present invention as set forth in the following claims.

I claim:

1. An implantable medical device comprising an outer housing, electronics within the outer housing, the electronics located on a substrate circuit board, and a rechargeable thin-film microbattery within the outer housing, the rechargeable thin-film microbattery having a solid-state electrolyte, wherein the rechargeable thin-film microbattery is devoid of liquids or other volatile materials from which the electronics must be protected, wherein the electronics are on a first face of the substrate circuit board, and the rechargeable thin-film microbattery is positioned adjacent to and having a portion directly below a second face of the substrate circuit board, the second face being on the side of the substrate circuit board opposite the first face.

2. The implantable medical device of claim 1, further comprising a back-up battery adjacent to the circuit board and the rechargeable thin-film microbattery.

3. The implantable medical device of claim 2, wherein a first group of the electronics is located on a first face of the substrate circuit board, and a second group of the electronics is located on the second face of the substrate circuit board.

4. The implantable medical device of claim 1, wherein a first group of the electronics is located on a first face of the substrate circuit board, and a second group of the electronics is located on the second face of the substrate circuit board.

5. The implantable medical device of claim 1, wherein the rechargeable thin-film microbattery lies in a plane that is parallel to the substrate circuit board containing the electronics.

6. The implantable medical device of claim 5, wherein there are two or more microbatteries that are stacked in series or in parallel.

7. The implantable medical device of claim 1, wherein there are two or more microbatteries that are stacked in series or in parallel.

8. The implantable medical device of claim 7, wherein the microbatteries are dynamically reconfigureable via programming of the device to provide a series connection, a parallel connection, or a combination of series and parallel connections.

9. An implantable medical device comprising an outer housing, electronics within the outer housing, the electronics located on a substrate circuit board, and a rechargeable thin-film microbattery within the outer housing, the rechargeable thin-film microbattery having a solid-state electrolyte, wherein the rechargeable thin-film microbattery is devoid of liquids or other volatile materials from which the electronics must be protected, wherein the substrate circuit board has a first face and a second face, and the electronics are located on the first face, and the rechargeable thin-film microbattery is deposited on the second face of the substrate circuit board.

10. The implantable medical device of claim 9, further comprising a back-up battery adjacent to the circuit board and the rechargeable thin-film microbattery.

11. The implantable medical device of claim 10, wherein a first group of the electronics is located on a first face of the substrate circuit board, and a second group of the electronics is located on the second face of the substrate circuit board.

12. The implantable medical device of claim 9, wherein a first group of the electronics is located on a first face of the substrate circuit board, and a second group of the electronics is located on the second face of the substrate circuit board.

13. The implantable medical device of claim 9, wherein the rechargeable thin-film microbattery lies in a plane that is parallel to the substrate circuit board containing the electronics.

14. The implantable medical device of claim 13, wherein there are two or more microbatteries that are stacked in series or in parallel.

15. The implantable medical device of claim 9, wherein there are two or more microbatteries that are stacked in series or in parallel.

16. The implantable medical device of claim 15, wherein the microbatteries are dynamically reconfigureable via programming of the device to provide a series connection, a parallel connection, or a combination of series and parallel connections.

17. An implantable medical device comprising an outer housing, the outer housing comprising at least one curved portion, electronics within the outer housing, the electronics located on a substrate circuit board, and a rechargeable thin-film microbattery within the outer housing, the rechargeable thin-film microbattery having a solid-state electrolyte, wherein the rechargeable thin-film microbattery is devoid of liquids or other volatile materials from which the electronics must be protected, wherein the rechargeable thin-film microbattery has a substantially oval shape that is adjacent to the substrate circuit board, wherein the electronics are on a first face of the substrate circuit board, and the rechargeable thin-film microbattery is positioned underneath a second face of the substrate circuit board, the second face being on the side of the substrate circuit board opposite the first face.

18. The implantable medical device of claim 17, wherein the rechargeable thin-film microbattery lies in a plane that is parallel to the substrate circuit board containing the electronics.

19. The implantable medical device of claim 17, wherein the device includes a back-up battery adjacent to the circuit board and the rechargeable thin-film microbattery.

20. The implantable medical device of claim 19, wherein a second group of the electronics is located on the second face of the substrate circuit board.

21. The implantable medical device of claim 19, wherein a first group of the electronics is located on the first face of the substrate circuit board, and a second group of the electronics is located on the second face of the substrate circuit board, and the rechargeable thin-film microbattery is located underneath or over the back-up battery, and both batteries are located adjacent to the substrate circuit board.

22. The implantable medical device of claim 17, wherein the electronics are located on at least a first face of the substrate circuit board and the rechargeable thin-film microbattery is positioned adjacent to the second face of the substrate circuit board and is adjacent to at least a portion of a back-up battery that is adjacent to the substrate circuit board.

23. The implantable medical device of claim 17, wherein there are two or more microbatteries that are stacked in series or in parallel.

24. The implantable medical device of claim 23, wherein the microbatteries are dynamically reconfigureable via programming of the device to provide a series connection, a parallel connection, or a combination of series and parallel connections.

25. The implantable medical device of claim 17, wherein the rechargeable thin-film microbattery is adjacent to at least a portion of a back-up battery that is adjacent to the substrate circuit board.

26. The implantable medical device of claim 17, wherein the rechargeable thin-film microbattery is positioned underneath a back-up battery that is adjacent to the substrate circuit board.

27. The implantable medical device of claim 17, wherein the rechargeable thin-film microbattery is positioned adjacent the second face of the substrate circuit board and at least a portion of a back-up battery that is adjacent to the substrate circuit board.

28. The implantable medical device of claim 17, wherein the rechargeable thin-film microbattery is positioned underneath a second group of electronics located on the second face of the substrate circuit board.

* * * * *